United States Patent
Brown et al.

(10) Patent No.: US 8,834,512 B1
(45) Date of Patent: Sep. 16, 2014

(54) NASAL DILATOR COMPRISING JOINED LEGS WITH END PADS AND AIR PASSAGES

(75) Inventors: Gregory A. M. Brown, Incline Village, NV (US); Brian A. Brown, Alamo, CA (US)

(73) Assignee: International Patent Development Group, LLC, Incline Village, NV (US)

( * ) Notice: Subject to any disclaimer, the term of this patent is extended or adjusted under 35 U.S.C. 154(b) by 385 days.

(21) Appl. No.: 13/100,514

(22) Filed: May 4, 2011

Related U.S. Application Data

(60) Division of application No. 12/332,310, filed on Dec. 10, 2008, which is a continuation-in-part of application No. 12/196,625, filed on Aug. 22, 2008, now abandoned, which is a continuation-in-part of application No. 11/954,961, filed on Dec. 12, 2007, now abandoned.

(51) Int. Cl.
*A61F 5/08* (2006.01)
(52) U.S. Cl.
USPC .. 606/199; 606/196; 128/206.11; 128/204.12
(58) Field of Classification Search
CPC ............ A61F 5/08; A61F 5/56; A61M 29/00; A61B 17/24; A61B 17/12104
USPC ............... 606/199, 157, 196, 204.45, 204.15; D24/190; 128/848, 206.11, 203.22, 128/200.24
See application file for complete search history.

(56) References Cited

U.S. PATENT DOCUMENTS

| | | | |
|---|---|---|---|
| 5,922,006 A * | 7/1999 | Sugerman | 606/204.45 |
| 6,328,754 B1 * | 12/2001 | Marten et al. | 606/199 |
| 6,631,714 B2 * | 10/2003 | Von Duyke et al. | 128/200.24 |
| 7,461,651 B2 * | 12/2008 | Brown | 128/200.24 |
| 2006/0085027 A1 * | 4/2006 | Santin et al. | 606/199 |
| 2006/0185676 A1 * | 8/2006 | Brown | 128/207.18 |
| 2006/0185677 A1 * | 8/2006 | Brown | 128/207.18 |
| 2006/0266367 A1 * | 11/2006 | Noce | 128/207.18 |
| 2009/0007919 A1 * | 1/2009 | Dolezal et al. | 128/206.11 |
| 2009/0054923 A1 * | 2/2009 | Benson | 606/199 |

* cited by examiner

*Primary Examiner* — Katherine Dowe
*Assistant Examiner* — Sidharth Kapoor
(74) *Attorney, Agent, or Firm* — David Pressman

(57) ABSTRACT

One embodiment of a nasal dilator comprises a pair of pads (100), supported by arms (110, 112) surrounding an air passage (115). Each arm has a bend portion (120) and a pad (121) that grips a wearer's septum (615). Leg portions (125, 125') extend down from the arms and are connected by a bight that surrounds the wearer's columella (620). The dilator is installed by gripping an optional handle (130) or the bight and inserting the pads and the arms into both nostrils. The dilator is urged upward and inward until the inner side of the bight touches the wearer's columella. To remove the dilator, the user grips the handle or bight and gently pulls downward until the dilator is removed. In an alternative embodiment, optional cushions (102, 122) soften the contact points between the dilator and the user's nasal structures and can supply medications through the user's nasal membranes.

20 Claims, 4 Drawing Sheets

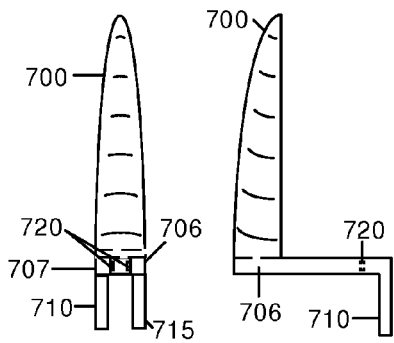
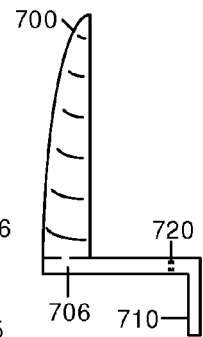
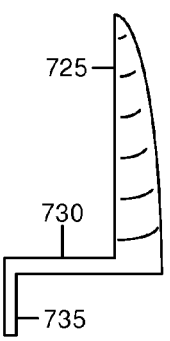
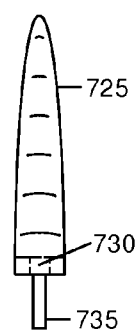
Fig. 7A   Fig. 7B   Fig. 7D   Fig. 7E
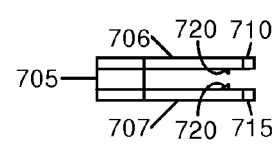
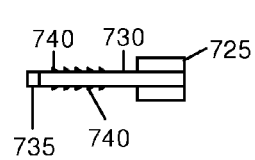
Fig. 7C   Fig. 7F
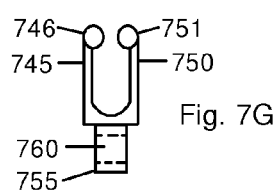
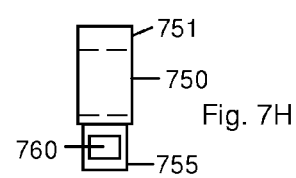
Fig. 7G   Fig. 7H
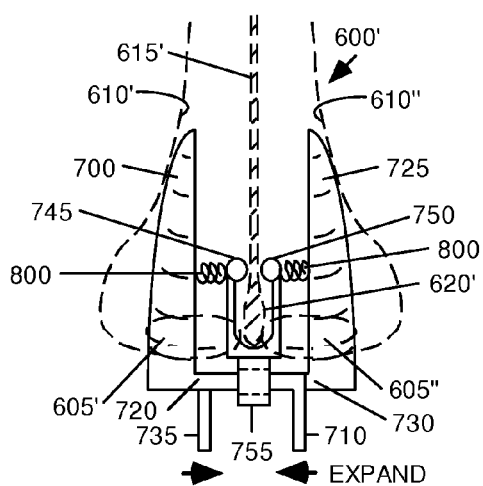
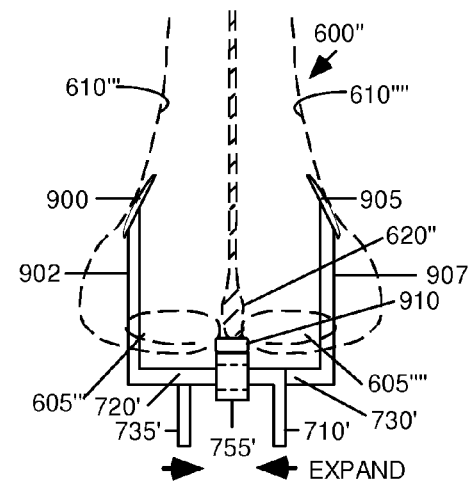
Fig. 8   Fig. 9

NASAL DILATOR COMPRISING JOINED LEGS WITH END PADS AND AIR PASSAGES

CROSS-REFERENCE TO RELATED APPLICATION

This application is a division of application Ser. No. 12/332,310, filed 2008 Dec. 10, which is a continuation-in-part (CIP) of application Ser. No. 12/196,625, filed 2008 Aug. 22, which in turn is a CIP of application Ser. No. 11/954,961, filed 2007 Dec. 12.

BACKGROUND

1. Field

The field is breathing aids, in particular intranasal instruments for dilating human nasal passages.

2. Prior Art Nasal Dilators

The following is a tabulation of some prior art (discussed below) that presently appears relevant:

| Pat. or Pub. Nr. | Kind Code | Issue or Pub. Date | Patentee or Applicant |
| --- | --- | --- | --- |
| 2,335,936 | B1 | Dec. 07, 1943 | Hanlon |
| 3,710,799 | B1 | Jan. 16,1973 | Caballero |
| 4,105,035 | B1 | Aug. 08, 1978 | Rella |
| 4,414,977 | B1 | Nov. 15, 1983 | Rezakhany |
| 5,479,944 | B1 | Jan. 02, 1996 | Petruson |
| 5,665,104 | B1 | Sep. 09, 1997 | Lee |
| 5,727,543 | B1 | Mar. 17, 1998 | Corsaro |
| 5,816,241 | B1 | Oct. 06, 1998 | Cook |
| 5,850,834 | B1 | Dec. 22, 1998 | Yoshida et al. |
| 5,895,409 | B1 | Apr. 20, 1999 | Mehdizadeh |
| 5,931,852 | B1 | Aug. 03, 1999 | Brennan |
| 5,931,854 | B1 | Aug. 03, 1999 | Dillon |
| 6,004,342 | B1 | Dec. 21, 1999 | Filis |
| 6,106,541 | B1 | Aug. 22, 2000 | Hurbis |
| 6,238,411 | B1 | May 29, 2001 | Thorner |
| 6,270,512 | B1 | Aug. 07, 2001 | Rittmann |
| 6,562,057 | B2 | May 13, 2003 | Santin |
| 6,626,172 | B1 | Sep. 30, 2003 | Karow et al. |
| 6,863,066 | B2 | Mar. 08, 2005 | Ogle |
| 6,962,156 | B2 | Nov. 08, 2005 | Michaels |
| 6,978,781 | B1 | Dec. 27, 2005 | Jordan |
| 7,055,523 | B1 | Jun. 06, 2006 | Brown |
| 7,105,008 | B2 | Sep. 12, 2006 | Maryanka |
| D430667 | S | Sep. 05, 2000 | Rome |
| 2001/0023695 | A1 | Sep. 27, 2001 | Auriemma |
| 2003/0181941 | A1 | Sep. 25, 2003 | Bruggisser et al. |
| 2004/0059368 | A1 | Mar. 25, 2004 | Maryanka |
| 2004/0111109 | A1 | Jun. 10, 2004 | Ruiz |
| 2004/0147954 | A1 | Jul. 29, 2004 | Wood |
| 2004/0237967 | A1 | Dec. 02, 2004 | Davis |
| 2004/0261791 | A1 | Dec. 30, 2004 | Horian |
| 2005/0247317 | A1 | Nov. 10, 2005 | Lockwood |
| 2006/0029653 | A1 | Feb. 09, 2006 | Cronk |
| 2006/0085027 | A1 | Apr. 20, 2006 | Santin et al. |
| 2006/0185676 | A1 | Aug. 24, 2006 | Brown |
| 2006/0259064 | A1 | Nov. 16, 2006 | Maryanka |
| 2006/0259065 | A1 | Nov. 16, 2006 | Maryanka |
| 2006/0266360 | A1 | Nov. 30, 2006 | Noce |
| 2006/0266367 | A1 | Nov. 30, 2006 | Noce |
| 2007/0006884 | A1 | Jan. 11, 2007 | Abramson |
| 2007/0028917 | A1 | Feb. 08, 2007 | Veeder |
| 2007/0157933 | A1 | Jul. 12, 2007 | Reed |
| 2007/0186930 | A1 | Aug. 16, 2007 | Davidson et al. |
| 2007/0255309 | A1 | Nov. 01, 2007 | Guyuron et al. |
| 2008/0119885 | A1 | May 22, 2008 | Yazdi |

3. Prior-Art Dilators

Mechanical dilation of nasal passages has long been used as a means for reducing snoring and obstructive sleep apnea (temporary cessation of breathing) in human subjects. Externally and internally applied forces have been applied to urge a portion of one or both of the outer walls of the nostrils to move in a direction away from the septum, thereby enlarging or dilating the nostrils and permitting freer flow of air through the nose. Rendering a person able to breathe freely reduces snoring and sleep apnea.

The following is a review of some prior developments and aids for dilating the nostrils.

Devices that Apply External Forces to Nostril

Some of the above references show devices that apply external forces to nostrils to dilate them.

Abramson shows an intraoral nasal dilator in combination with a mandibular repositioner. A device inserted inside a wearer's upper lip stretches the tissue of the lip and lateral nasal walls, thereby preventing collapse of the nostrils during respiration.

Davidson et al. show a breathing arrangement comprising a headgear assembly. The assembly includes nozzles that are inserted into a person's nose and an optional component that covers the mouth. The nozzles are connected by a hose to an air or gas supply. Thus users of the assembly are made to breathe primarily through their nose.

While the foregoing arrangements are useful, they are bulky and require installation by knowledgeable technicians. In addition, they are neither inexpensive nor disposable.

Horian, Lockwood, Cronk, Dillon, and Johnson, all teach variations on adhesive strips that are applied to the outer surfaces of both nostrils. The strips are interposed between the nostrils and a springable elastic member that urges the outer surfaces of the nostrils in a direction away from the nasal septum, thereby dilating the nostrils.

Veeder teaches an alternative adhesive strip that is usable on a single nostril. This strip is adhesively secured between the outside of the wearer's nostril and the proximate cheek, thereby allowing the user to adjust the tension on the nostril.

While these adhesive arrangements are useful, they normally require the user to first clean away oils on the skin in order for the adhesive to remain in place. They also block normal breathing of the skin and may lose their adhesive tack as the user perspires.

Ruiz shows a prosthesis that resides both outside and inside the wearer's nostrils. The prosthesis is made of a rigid and elastic material, such as metal wire. It is formed to rest on the nasal dorsum and reach around the outside of the nose into each nasal vestibule, springably spreading the vestibules and urging the outer nostril walls away from the septum. Ruiz asserts that the device may be wearable during sports activities, but since it resides partially outside the wearer's nose, it may easily become dislodged in some activities.

Hurbis shows a surgically implantable nasal dilator that is placed within the nasal tissues. The device is V-shaped. The vertex of the V is placed about one-third of the distance from the tip to the bridge of the nose. The arms of the V extend downwardly over the vestibules of the nostrils, imparting an oppositely-directed opening force on the wall tissues of the nose. Since this device requires surgical implantation, it cannot be simply inserted by an untrained user.

Devices that Apply Dilating Forces from within Nostrils

Others of the above references show devices that apply dilating forces from within nostrils.

Rella shows an apparatus that is inserted within one nostril to alleviate breathing difficulty created by a deviated septum. In one embodiment, device comprises two straight rails that are joined and separated by two rods. A first rail is approximately one-half the length of the nasal septum. A second rail is about three-fourths as long as the first rail. Both rails include a series of holes for installation of the ends of the rods. As the device is inserted into a nostril about one-third of the distance from the entrance of the nasal vestibule to the bridge of the nose, the first rail is placed against the nasal septum and the second rail is placed against the inner nostril wall. The two rails are held apart by rods of predetermined lengths inserted into the holes in the rails. The device widens the nostril and also straightens the septum over time. This device requires expert installation and monitoring to ensure its proper operation.

Numerous prior-art devices insert nominally spherical, cylindrical, annular, or conic sections into one or both nostrils. The purpose of these sections is to enlarge the area adjacent the nasal vestibule in order to improve breathing through the nose.

Rome shows a pair of conic sections joined by a U-shaped wire. The sections are insertable into the nasal vestibules and are held in place by the wire.

Caballero shows a pair of open, nominally spherical cages that are joined together by a flexible chain. The cages are sized to bear against the septum and displace the outer walls of the nostrils. Air can freely pass through the cages. The chain limits the insertion distance and facilitates removal of the cages.

Lee shows a nasal dilator device comprising two thin-walled, rigid, right-circular cylinders. The cylinders are fixed to each other by a connecting strip at their bases. The cylinders are inserted into both nostrils a distance that is limited by the connecting strip as it contacts the outer bottom of the nasal septum. A tab, located at the center of the connecting strip, depends downward to facilitate removal of the cylinders.

Similar arrangements having various shapes are shown by Mehdizadeh, Filis, Santin, Jordan, Maryanka '008, Wood, Santin et al., Noce (two applications), and Reed.

Michaels (two patents) shows a pair of partially closed, porous cylinders similar to the above. These cylinders are used to filter the air entering the nasal airway.

A single nostril dilating device is taught by Hanlon. This device is roughly a conic section closed at the narrow end and containing an entrance orifice and series of perforations along its walls. Air enters the entrance and passes through the holes into the user's nasal cavity, permitting normal breathing. The walls of the device adjacent the entrance are partially removed to permit the user's nose hairs to grow there.

Rezakhany shows a nasal dilator comprising a pair of roughly axially-aligned rings that are connected and separated by two struts. One ring is smaller than the other. The smaller ring is sized and shaped to fit comfortably in the nasal ostium and the larger ring is sized and shaped to fit comfortably in the nasal vestibule. The axis of the ring assembly is coincident with the axis of the nostril and the rings are sized to dilate the nostril as required for normal breathing.

Davis shows a pair of flexible, tubular structures that are inserted into the nostrils. The tubes are joined by a bridge that determines the limit of insertion as it rests against the lower, outer portion of the nasal septum. The diameters and shapes of the tubes as well as their positions urge the nasal passageway walls apart, thereby improving breathing by increasing the overall diameter of the nostrils.

Petruson shows a U-shaped device comprising a pair of tabs joined by a resilient connecting member. The connecting member is bent into a curved shape by squeezing the arms of the U together. The arms of the U are then inserted into the nostrils. When the squeezing force is removed, the arms of the U spread outward, thereby expanding the nostrils.

Cook shows a nasal dilator comprising a V-shaped spring arrangement. Spiral spring coils are located at the tips of the arms of the V. The arms of the V are formed from the same spring material. For insertion, the two tips of the V are squeezed together and inserted into both nostrils until the base of the V is in contact with the outer bottom of the nasal septum. When the arms of the V are released, they force the nostril walls outward, enlarging the nostrils and permitting normal breathing.

Ogle shows a pair of springably connected loops oriented in a V-shape and connected by a junction at the base of the V. The loops are sprung together and inserted in the nostrils to a depth determined by the distance between the top of the loops and the base of the V. When they are released, the loops force the nostril walls outward, thereby opening the nostrils for improved breathing. In addition, a filter arrangement can be affixed at the base of the V, providing a filtering function.

Karow et al. show a device comprising an elastically deformable, nearly flat plate, approximately one cm in width and one-half centimeter in height. The plate optionally accommodates insertion of a rod at its central point in order to facilitate insertion into and removal from a nostril. For insertion, the plate is bent into a curve by forcing the wide ends toward one-another. The curved plate is then inserted into a nostril a distance about equal to its height. When inserted, the plate is allowed to attempt to return to its original nearly flat state. In so doing, the plate enlarges the nostril, permitting normal breathing.

Thorner shows a device similar in concept to those of Cook and Ogle above, except it is held in place by a conjoined, nearly parallel external strap that is secured to the wearer's face by adhesive strips.

Rittman shows a roughly U-shaped, bent-wire nasal dilator similar to those of Cook and Ogle, with the addition of a catch or ratchet. The ends of the arms of the U press outward on the nostril lining while the catch portion extends inwardly toward the septum. The catch is of sufficient length to reach but not contact the septum. It engages the columella, i.e. the fleshy, lower widened base of the nasal septum, i.e., the portion of the septum that one sees when looking at a person's nose from the outside. The dilator's grip of the columella prevents unwanted ejection of the dilator.

Those devices that have no other restraining means and engage neither the septum nor the columella are at risk of being dislodged during use, for example during a vigorous sneeze. The following devices at least grip the septum for retention in the nose.

Corsaro shows a U-shaped, wireform nasal dilator with looped arms. The outer portion of the loops urge the outer walls of the nostrils in a direction away from the septum. The inner portion of the loops rest against the septum, and in addition engage the columella to prevent unwanted ejection of the dilator.

Brennan shows a nasal dilator that operates in a manner similar to that of Karow et al. Brennan's dilator comprises a U-shaped portion that terminates in flexible, semi-circular arms. The arms urge the nasal walls outward while the U-shaped portion rests against the septum. The dilator widens at the base of the U to include a portion that engages the columella and prevents unwanted ejection of the dilator.

Yoshida et al. show a U-shaped respiration aiding device. The upper end of the U is inserted into the nose until the base of the U meets the columella. The arms of the U widen at the position of the nasal vestibule, forcing the nostrils open. The tops of the arms curve inward and engage the septum to secure the device. A pair of magnets, oriented to attract one-another, are included in the tops of the arms to more firmly hold the device in place by gripping the septum.

The Brown patent and published application shows a dilator comprising a U-shaped portion with outwardly extending arms at its upper end. The arms terminate in pads that press against the outer walls of the nostrils, forcing them outward. Thickened portions of the arms at the upper ends of the U press against the septum and also engage the columella to prevent unwanted ejection of the device. Brown's dilator also optionally stores and delivers chemical compounds.

Bruggisser et al. show a device similar in construction to Brown, except the arms extend from the lower end of the U, rather than the upper end.

The pads in both Brown and Bruggisser are supported by single, relatively thin arms which could break in the event of a blow to the wearer's nose.

From the above it is evident that although they may ease breathing to a degree, the prior-art devices suffer from various deficiencies.

Advantages

Accordingly some advantages of various aspects of our device are to provide an inexpensive and disposable dilator that is rugged, that is not bulky, that can be installed by a lay person, is not easily dislodged, is unobtrusive, does not require surgical implantation, and does not require monitoring during use. Other advantages will become apparent from a review of these and other aspects and embodiments described below.

SUMMARY

In accordance with one preferred embodiment of one aspect, a human nasal dilator comprises a roughly U-shaped device. The lower portions of the arms of the U curve inward to surround the columella and grip the septum. A ring-shaped air passage orifice extends upward from the top of each lower portion of the U, and a pad extends upward from the top of the orifice. The pads and the outer walls of the orifice both urge the nostril walls outward, away from the septum, thereby permitting greater air flow through the nose. An optional tab extends downward from the bottom of the U to facilitate insertion and removal of the dilator. A first alternative embodiment incorporates soft cushions on the pads to improve the wearer's comfort. Second and third alternative embodiments add a ratchet mechanism to permit adjustment of the forces applied to the nostril walls by the dilator.

DRAWING FIGURES

FIGS. 7A through 7H show the components of an alternative embodiment where a dilator has dilating arms that are slidably mounted with respect to each other FIG. 8 shows the embodiment of FIGS. 7A-7H in place in a wearer's nose.

FIG. 9 shows an alternative embodiment where a dilator has relatively small intranasal pads and is in place in a wearer's nose.

FIGS. 16-18 show a sixth alternative embodiment where a dilator has pads with a bifurcation

Figure 1:
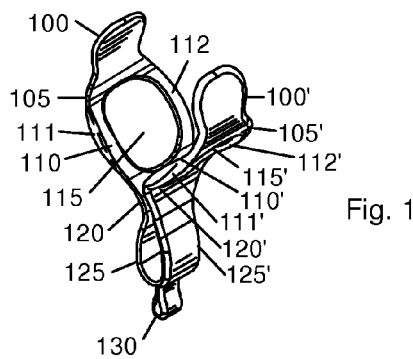
FIG. 1 is a perspective view of one preferred embodiment of a dilator secured by combination of forces against the septum, the columella, and the outer lining of the nostril walls.
Figure 2:
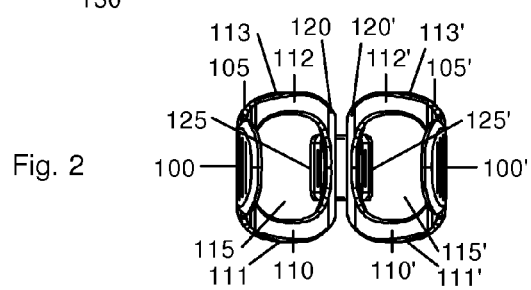
FIGS. 2 through 5 are respectively top, front, bottom, and side views of the dilator of FIG. 1.

| Reference Numerals | | | |
|---|---|---|---|
| 100 | Pad | 102 | Cushion |
| 105 | Bend | 110 | Arm |
| 111 | Surface | 112 | Arm |
| 113 | Surface | 115 | Passage |
| 120 | Bend | 121 | Pad |
| 122 | Cushion | 125 | Vertical section |
| 130 | Handle | 600 | Nose |
| 605 | Nostril | 610 | Wall |
| 615 | Septum | 620 | Columella |
| 700 | Member | 706 | Rail |
| 707 | Rail | 710 | Handle |
| 715 | Handle | 720 | Tooth |
| 725 | Member | 730 | Rail |
| 735 | Handle | 740 | Teeth |
| 745 | Arm | 746 | Ball |
| 750 | Arm | 751 | Ball |
| 755 | Portion | 760 | Opening |
| 800 | Spring | 900 | Pad |
| 902 | Arm | 905 | Pad |
| 910 | Pad | 1000 | Band |
| 1400 | Notch | 1405 | Notch |
| 1410 | Notch | 1500 | Bifurcation |
| 1505 | Notch | 1600 | Arrow |

DETAILED DESCRIPTION

First Embodiment—FIGS. 1 to 5—Dilator Secured by

Combination of Forces Against Septum, Columella, and Outer Lining of Nostril Walls FIGS. 1 through 5 respectively show perspective, top, front, bottom, and side views of a first embodiment of a dilator that comprises a single piece or strip of material (metal or plastic) that is roughly U-shaped and is shown inverted. The left and right sides or legs of the U are identical and symmetrically located about the vertical centerline of the U. The parts on the left side of the dilator are identified with non-primed numbers and are identical to those on the right side, which are primed. Primed and unprimed parts are sometimes simply referred to by their unprimed number.

The dilator comprises a pair of sections 100 and 100' which are slightly bent in at the upper ends of the legs of the U. Sections 100 and 100' will be referred to as upper or outwardly facing pads since each presses against the inside of an outer wall of a nostril. Pads 100 can be rectangular, oval, circular, or of any other suitable geometry. Each arm has a first convex bend 105 adjacent the pad. Then, looking at the left leg of the U in FIG. 1, the dilator has a pair of inwardly extending arms 110 and 112 that surround and define an opening or air passage 115. The right or closer leg in FIG. 1 is a mirror version of the left leg and has arms 110' and 112' that surround and define an opening or air passage 115'. Passages 115 are shown as rectangles with rounded corners, but they can have any other suitable shape, such as oval, intersecting ovals, circles, etc.

Then the legs each have a concave bend 120 and a bottom portion or vertical section 125. Sections 125 and 125' are joined by a bottom bight portion. An optional handle 130 extends from the bottom of the bight portion. The outer portions of arms 110 and 112 include flat or gently curved surfaces 111 and 111' and 113 and 113'. These surfaces lie in a plane roughly parallel to the axis of passages 115, and have sufficient surface area to provide a dilating force, yet minimize pressure on the nasal passages, thereby improving wearer comfort. As shown, starting from the bight, the bottom portions 125 of the legs are spaced apart. Then each leg has a first, inward curve followed by a second outward curve that together provide a lower or inwardly facing pad or bend that is concave as seen from the outside and convex as seen from the inside. The second outward curve is followed by a third, inward curve so that the second and third curves provide an upper or outwardly facing pad or bend that is concave as seen from the inside and convex as seen from the outside. As shown, the curves and bends are smooth and continuous.

Figure 6:
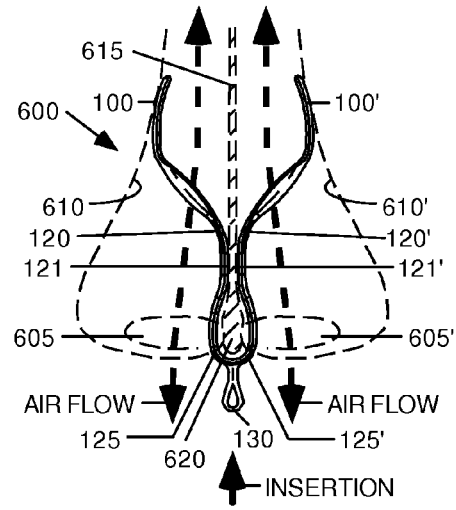
FIG. 6 shows a frontal view of the embodiment of FIGS. 1 through 5 in place in a wearer's nose.

Pads 100 curve inward to conform to the shape of the inner wall of a properly dilated nostril 605 (FIG. 6). Arms 110 and 112 are joined to pads 100 at bends 105, which have a nominal interior angle of 150 degrees, although other angles can be used, depending upon the shape of the wearer's nose. The other ends of arms 110 and 112 are joined to vertical sections 125 at bends 120, having a nominal interior angle of 160 degrees. Again, other angles can be used, depending upon the shape of the wearer's nose. In one aspect, the material comprising the dilator can be bent, either by forcing or by heating, then bending, then cooling, so that the above angles can be adjusted to fit individual noses.

Handle 130, as stated, is joined to the bight portion joining sections 125 and 125'. The handle is an optional folded strip with its own bottom bight portion; it can be any length and shape. E.g., it can be sized and shaped to extend to and lie over the wearer's upper lip where it can be secured with adhesive tape, if a wearer has unusual anatomy that makes this necessary.

The dilator is preferably made from a flexible, resilient plastic material such as polycarbonate, although other materials such as metal and wood, or a combination of plastic, metal, or wood or any other suitable material can be used. If plastic is used, it can be either a thermosetting (such as polycarbonate) or a thermoplastic material (such as methyl methacrylate polymer). In the case of a thermoplastic material, a user can heat the dilator to its plastic temperature, then manually alter its shape for a custom fit. In addition, the plastic material can optionally be porous in order to prevent occlusion of air and moisture from reaching and leaving the nasal lining. Pores in the plastic material can optionally be pre-filled with odorants or medications.

The dilator ranges in height between 1.25 and 3.6 cm (0.5 and 1.5 inch), and width from 0.5 to 3 cm (0.25 to 1.25 inch), depending on the size of the wearer's nose. Various sizes may be provided, e.g., extra small, small, medium, and large to accommodate different nose sizes. The thickness preferably ranges between 0.05 and 0.6 cm (0.020 and 0.125 inch). All sharp edges are eliminated or rounded. In addition, areas applying opening forces to the nostril are increased in size to increase pad-like bearing areas, thereby distributing the load over larger areas and reducing pressure on the nose in order to prevent harm to the wearer's nostril lining.

First Embodiment

Operation—FIG. 6

FIG. 6 shows a frontal view of the dilator fully inserted and in use in a wearer's nose. The nasal structures affected by insertion of the dilator include the nostrils 605 and 605', the outer nostril walls 610 and 610', the septum 615, and the columella (the fleshy, lower widened column at the base of the nasal septum, i.e., the portion of the septum that one sees when looking at a person's nose from the outside) 620. To use the dilator, the wearer grips handle 130, or the bight at the bottom of the dilator if no handle 130 is used, inserts tabs 100 and 100' into nostrils 605 and 605', and gently urges the dilator inward until the inside of the bight—the junction of vertical sections 125 and 125'—rests against columella 620. At this point, pads 100 and 100' springably press against outer nasal walls 610 and 610', urging them outward, away from septum 615, thereby enlarging the airway path of the nostril and easing the wearer's breathing as air freely flows through passages 115 and 115' (FIG. 1).

Pads 100 and arms 110 and 112 are springy, or rigid, depending upon the material used. The arms urge the pads to press against the circumference of the nasal walls, urging them open and preventing the nostril walls from collapsing toward or against the septum. Such collapsing tends to occur when one inhales rapidly through the nose, causing the pressure to drop and the walls to move inwardly, as when one sniffles or breathes in too rapidly for the size opening available. At bends 120 and 120' the dilator curvably extends into another pair of pads 121 and 121' which gently press against septum 615. The springable forces pressing against the outer nasal wall by pads 100 and 100' are coupled through arms 110, 110', 112, and 112' and are applied to septum 615 at pads 121 and 121' on either side of septum 615. This pinching of septum 615 causes the dilator to resist unwanted ejection by virtue of friction between the dilator and septum 615.

In addition, the pressing of pads 121 and 121' against septum 615 provide a counterbalancing force against each other that applies all the springable force from pads 100 and 100' against nasal walls 610 and 610', thereby maximizing the opening force. Pads 100 and 100' contribute additional frictional forces by pressing against walls 610 and 610'. In addition, the dilator necks inward at bends 120 and 120' and pads 121 and 121' with force from the springable force from the dilator. This further ensures its retention by engaging columella 620, which is slightly wider. The outward forces applied by surfaces 111, 111', 113, and 113' also contribute additional frictional forces by pressing against the internal walls of the nostril, holding them open and further securing the dilator in place and preventing unwanted ejection.

To remove the dilator, the wearer grips handle 130, or the bottom bight if no handle is used, and gently pulls downward, away from the nose in a direction parallel to the septum.

First Alternative Embodiment

Figure 3:
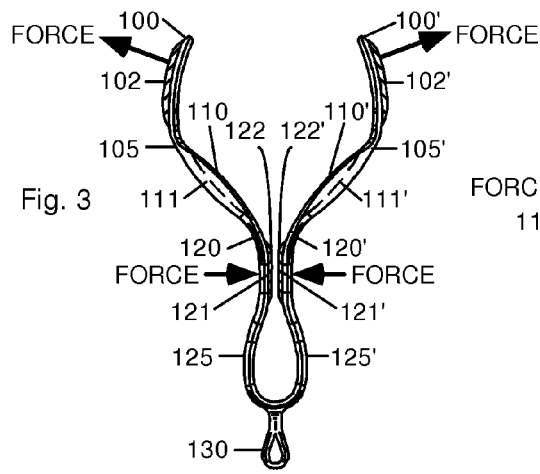
Figure 5:
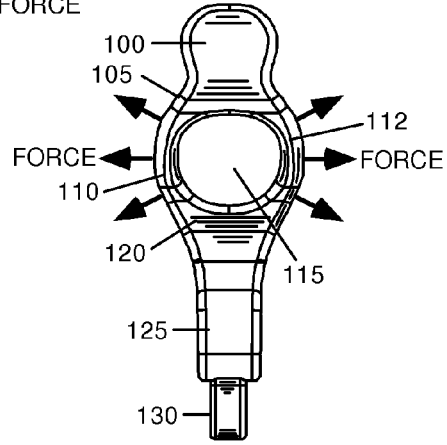
Figure 4:
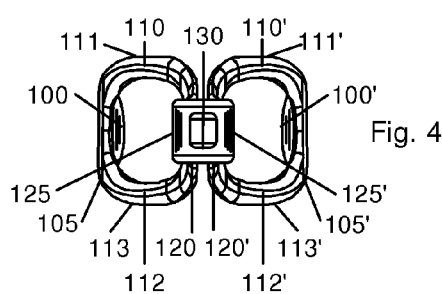
Figures 10, 11:
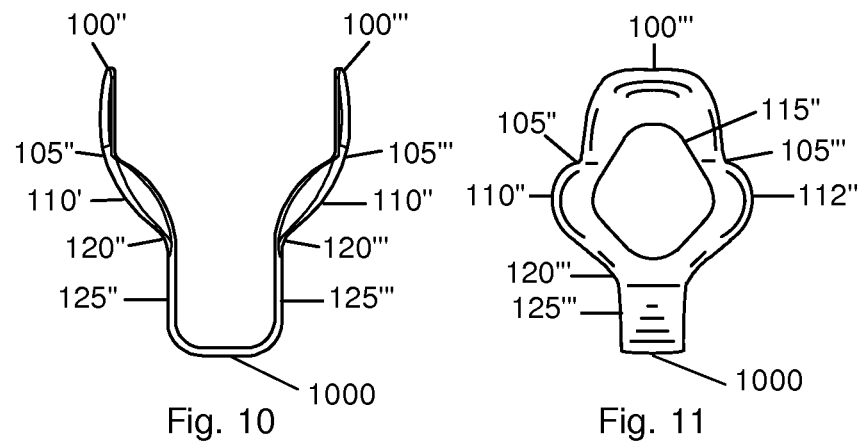
FIGS. 10-14 show a fourth alternative embodiment where a dilator has straight legs joined by a flat band.
Figures 12, 13:
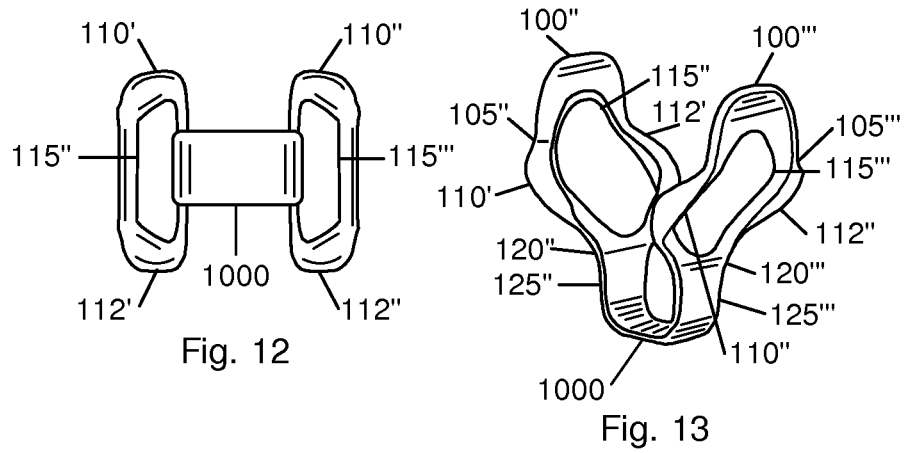

Description—FIG. 3—Cushions Added to Surfaces in Contact with Nasal Tissues

FIG. 3 is a front elevation view of the dilator. In order to further protect the nasal linings, optional cushions 102 and 102' can be added to pads 100 and 100'. Similarly, optional cushions 122 and 122' can be added inside pads 121 and 121' to protect septum 615. In addition, cushions can be applied to surfaces 111, 111', 113, and 113'. These cushions can be made of silicone rubber, caoutchouc (rubber), soft plastic, plastic foam, or foam rubber or any other suitable material. The cushions can optionally contain medications (not shown) that will diffuse into the wearer's nasal walls 610 and 610' by virtue of contact between the two.

Second Alternative Embodiment

Description—FIGS. 7A-7F and 8—Dilating Arms Slidably Mounted with Respect to Each Other FIGS. 7A through 7H show another or second embodiment of a dilator comprising separate left and right portions which each have a center portion that extends to and interfits with the other portion. FIGS. 7A, 7B, and 7C, respectively, show side, front, and bottom views of the left-hand portion. A vertical member 700 extends upward from the left end of a horizontal rail portion having rails 706 and 707 which form a gap therebetween. Member 700 has a curved shape to conform to the shape of the wearer's outer nostril wall and to maximize nostril area for improved air flow (FIG. 8). A pair of handles 710 and 715 extend downward from rails 706 and 707, respectively. One or more ratchet teeth 720 extend inward from rails 706 and 707 (FIG. 7C).

FIGS. 7D, 7E, and 7F, respectively, show front, side, and bottom views of the right-hand portion of this embodiment. A vertical member 725, similar to member 700 (FIG. 7A), extends upward from one end of a horizontal rail 730. A handle 735 extends downward from rail 730. A series of ratchet teeth 740 protrude from rail 730. Rail 703 is designed to fit in the gap between rails 706 and 707 of the left portion.

FIGS. 7G and 7H show front and side views of the central portion, which comprises a pair of pinching arms 745 and 750 that extend upward from a lower portion 755. Arms 745 and 750 terminate in inwardly-located balls 746 and 751 respectively. The bottoms of the arms are joined by a bight atop portion 755. Portion 755 has a through-hole 760.

This embodiment is of approximately the same size as the previous embodiment and is made of similar materials.

Second Alternative Embodiment

Operation—FIG. 8

FIG. 8 shows frontal view of a wearer's nose 600' with nostrils 605' and 605", nasal walls 610' and 610", septum 615', and columella 620', and a dilator in place. Rails 720 and 730 have been inserted through opening 760 in portion 755.

The dilator of this embodiment is initially supplied with rail 730 inserted into the gap between rails 706 and 707 with vertical members 700 and 725 at rest as close as possible to each other. In this position, handles 710 and 735 are at their maximum separation.

To use the dilator, the wearer inserts members 700 and 725 into nostrils 605' and 605", respectively, until the bight portion of the dilator rests against columella 620'. Balls 746 and 751 at the ends of arms 745 and 750 may touch septum 615' and will surround columella 620, ensuring that the dilator will not be unintentionally ejected from nose 600'. Then the user gently squeezes handles 710 and 735 together, forcing members 700 and 725 apart until the desired amount of dilation of walls 610' and 610" is reached. As rail 730 moves within the gap between rails 706 and 707, ratchet teeth 720 (FIG. 7C) successively engage teeth 740 (FIG. 7F), preventing reverse motion and thereby securing the dilator.

As with the first embodiment, the outer surfaces of portions 700 and 725 can optionally be padded. In addition, an optional pair of springs 800 can be added to increase the force applied to walls 610' and 610" by members 700 and 725.

The present embodiment is of approximately the same size as the previous embodiments and is made of similar materials.

Third Alternative Embodiment

Description and Operation—FIG. 9—Relatively Small Intranasal Pads

FIG. 9 shows a frontal view of a wearer's nose with a dilator in place. This dilator has relatively small intranasal pads and a reduced securing force, which is appropriate for some users with smaller anatomy. Vertical members 700 and 725 (FIG. 8) are replaced by pads 900 and 905 that extend from arms 902 and 907 which extend upward from rails 720' and 730'. Installation of the dilator of this embodiment is the same as in the previous embodiment; pads 900 and 905 and arms 902 and 907 are inserted through nostrils 605''' and 605''''. After the user fully inserts the dilator, they squeeze handles 710' and 735' together, forcing pads to move outward against outer nostril walls 610''' and 610'''' of nose 600".

This embodiment further includes an adhesive pad 910 to ensure retention of the dilator. Pad 910 can be a piece of "double-stick" foam tape, i.e. tape with adhesive layers on both sides. Instead of being held in place by the ends of arms 745 and 750 (FIG. 8), the dilator is held in place by pad 910 that is secured between ratchet-housing portion 755 and the wearer's columella 620".

Fourth Alternative Embodiment

Description and Operation—FIGS. 10-14—Straight Legs Joined by a Flat Band

FIGS. 10-13 show front, side, bottom, and perspective views, respectively of a fourth alternative and currently preferred embodiment. This embodiment comprises a flat band 1000 at the bottom that joins vertical sections 125" and 125'''. Sections 125" and 125''' are straight, instead of curved. Arms 110 and 112 are joined by a pair of rounded, rectangular pads 100 at their upper ends. From there, arms 110 and 112 depend downward through a first, inward bend 105, then join with vertical sections 125 after passing through a second, downward bend 120. Air passages 115" and 115''' are formed within the space between arms 110 and 112. Passages 115 each comprise four rounded corners and four straight sides, where adjacent sides are oriented at an angle, as would be formed by two intersecting oval shapes oriented at right angles with one-another. This embodiment can be made from any of the materials used in the first embodiment.

To insert this embodiment, the user grips sections 125" and 125''', squeezing them together sufficiently to permit insertion of pads 100 and arms 110 into their respective nostrils (not shown). The user then continues inserting the dilator until band 1000 is in contact with their columella. Legs 125 are spaced sufficiently that they can lightly contact the wearer's columella and septum. Frictional forces between the user's nasal lining, and arms 110" and pads 100''' are sufficient to hold the dilator in place without unwanted ejection of the dilator. In addition, resistive pressure from nasal walls on pads 100" transfer through arms 110''' and apply a bending force to sections 125" and 125''' which in turn apply pressure against the nasal septum, also creating more frictional fit. Enlarged surface areas 110' and 110" and 112' and 112" outside the open airway also create outward force on the nasal lining to maintain an open airway and this results in additional frictional force to resist ejection of the device.

Figure 14:
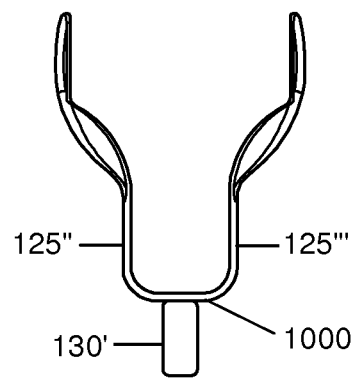

FIG. 14 shows front elevation view of a dilator having an optional handle 130' attached to band 1000. Some users may find this aspect of the embodiment more convenient to use since it provides additional gripping space for insertion and removal of the dilator.

Fifth Alternative Embodiment

Description and Operation—FIGS. 15-18—Notched Bight

Figure 15:
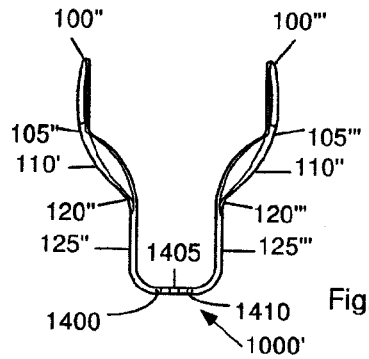
FIGS. 15-18 show a fifth alternative embodiment where a dilator has a notched bight section.
Figure 16:
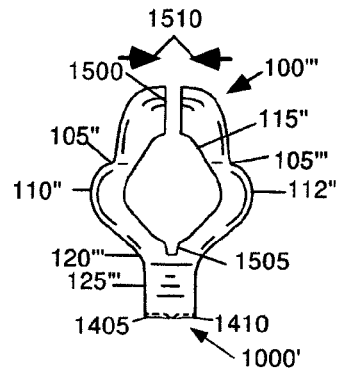
Figure 17:
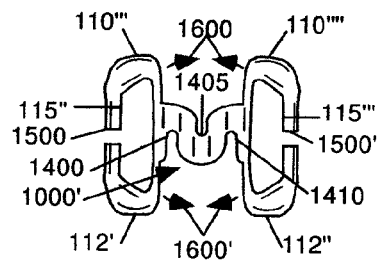
Figure 18:
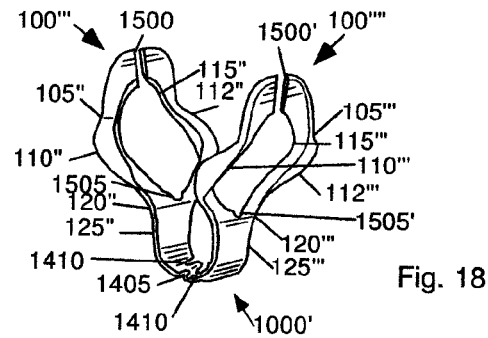
Figure 20:
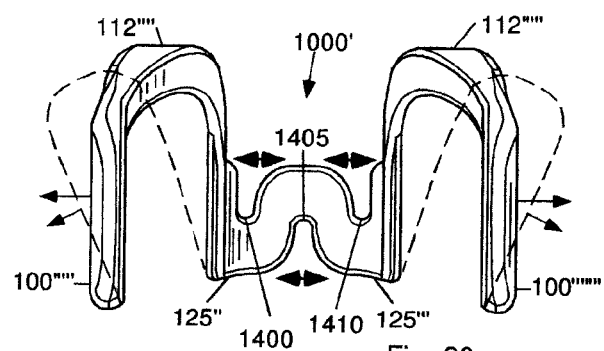

FIGS. 15-18 respectively show front elevation, side, bottom, and perspective views of a dilator according to various aspects of 5$^{th}$ and 6$^{th}$ alternative embodiments. FIGS. 15-18 show a 5$^{th}$ alternative embodiment and FIGS. 16-18 show both the 5$^{th}$ and a 6$^{th}$ alternative embodiments. In these embodiments, which are similar to the fourth alternative embodiment (FIGS. 10-13), a series of notches 1400, 1405, 1410, are added to the bottom band or bight portion 1000' that joins vertical sections 125" and 125'". Notches 1400-1410 and their operation are shown in detail in the bottom view of FIG. 20. Their presence permits the dilator to comfortably fit into nostrils (not shown) having various anatomical configurations.

Most nostrils, when seen from the bottom, are elongated from front to back and are parallel. However some are oriented at an angle to each other so that they form a V with the pointed base of the V at the front. To accommodate such a V-shaped nostril pair, the legs of the dilator are bent with the aid of the notches so that, instead of being parallel when seen from the bottom, as in FIG. 12, they form an angle with the apex to the front. Other nostril configurations that the dilator can be bent to accommodate with the aid of the notches are those with a deviated septum, for example.

The depth of notches 1400-1410 is preferably equal to one-half the width of the bight, although other depths can be used. The sides of the notches can be either springably or permanently squeezed together or pulled apart, depending upon the choice of materials used, i.e. flexible, rigid, or thermoplastic, in order to rotate sections 125" and 125'" about their axes, as indicated by arrows by the single and double arrows and dashed lines in FIG. 20.

Sixth Alternative Embodiment

Description and Operation—FIGS. 16-18—Bifurcation in Pads

The embodiment of FIGS. 16 to 18 has an additional feature that permits adjustment of the width of the dilator. A bifurcation 1500 separates the two portions of pads 100'" and 100"" at their upper ends. A notch 1505 extends the length of arms 110" and 112" at the bottom of passage 115" where the arms join legs 125" and 125'", in the region of bend 120'". Extending the notch 1505 into this region increases its flexibility and permits gentle, springable narrowing of the width of the dilator when arms 110" and 112" are urged together by contact with the interior of the nostril (not shown), as indicated by arrows 1510 (FIG. 15).

Seventh Alternative Embodiment

Description and Operation—FIGS. 19-22—Pads Held by Single Arms and Notched Bight FIGS. 19-22 show a seventh embodiment having yet a different configuration that is suitable for nostrils of still other anatomical configurations. This embodiment contains some structural elements of the fourth through sixth embodiments, while removing others.

FIGS. 19-22 are respectively front elevation, top, side, and perspective views of the seventh embodiment. While the fourth and fifth embodiments had two arms 110 and 112 that formed a bifurcation and defined an passage therebetween, in this embodiment arm 110 has been removed, leaving only one remaining arm 112"" (left) and 112""' (right) that extends over part of the interior of the wearer's nostril (not shown) in a manner similar to arm 112 of the preceding embodiments. Removing arm 110 narrows the legs of the dilator and permits the dilator to be inserted into nostrils (not shown) that have different nasal configurations and/or provides easier insertion and removal and greater comfort than the larger embodiments. Remaining arm 112 curves around and defines an air passage similar to that formed by the bifurcation (arms 110 and 112) of the previous embodiments, except that there is no arm on one side of the air passage. Arm 112 extends around the bottom, one side, and top of the air passage. The shape of the defined air passage in each nostril is roughly a long oval but can have various other shapes by varying the shape of arm 112.

Figure 21:
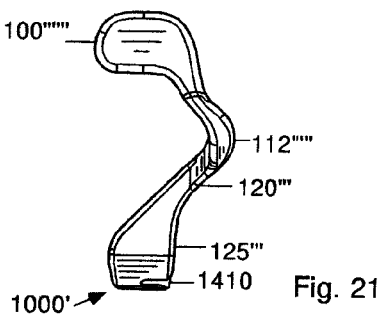
Figure 22:
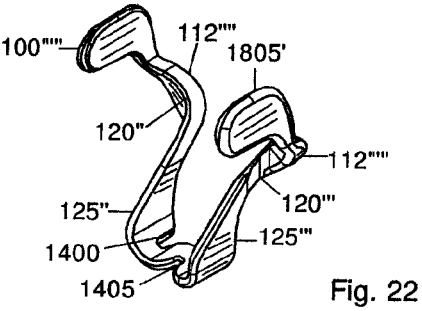

As with the preceding three embodiments, the present dilator has a flat band, bottom, or bight section 1000' at its bottom end. Vertical legs 125 on either side of band 1000' extend up at substantially right angles from the bottom or bight section. Note as shown that each leg 125 has four sections that extend progressively upward from the bottom: A first or bottom section extends up substantially vertically from the bottom and is parallel to the leg on the other side of the bottom. Then a second section extends up from the bottom section and slopes backwardly at an acute angle to the vertical but is still parallel to the other leg. Then each leg has a third second section that extends up from the second section and curves outwardly and continues sloping backwardly at bend 120 and then curves forwardly at arms 112 so as to form a rearwardly extending bend as best seen in FIG. 21. Then the legs have a fourth section that extends up from the third section and further forwardly and substantially vertically upward and widens forwardly and upwardly to form parallel (FIG. 19 and FIG. 21) pads 100. I.e., at the tops of the legs, arms 112"" and 112""' respectively support pads 100""" and 100"""' at the upper end of the dilator (FIG. 22).

Figure 19:
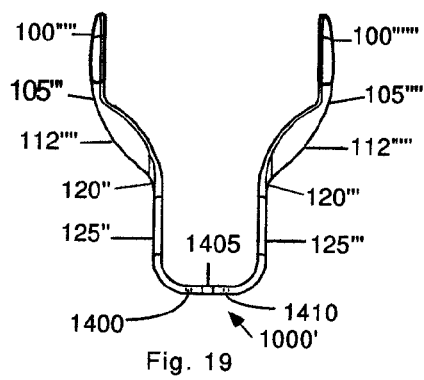
FIGS. 19-22 show a seventh alternative embodiment where a dilator has pads held by single arms and a notched bight section.

Thus as show in FIGS. 19 to 22, the dilator comprises an elongated, flexible having a sheet or ribbon configuration with two opposing parallel sides that are relatively close together and two opposing edges that are relatively widely spaced. One of the sides is outwardly facing and the opposite is inwardly facing. The member is substantially U-shaped when seen from a front side (FIG. 19). The member has a generally horizontal and substantially flat bottom section 1000. The inwardly facing side of the bottom section faces upwardly and the outwardly facing surface faces downwardly when the member is inserted into the nostrils. The two legs extend upwardly from the bottom section and are each are substantially longer than the bottom section, generally vertically oriented, and have a free upper end. Each leg has four parts (FIG. 21): (1) a first part that extends upward at a substantially right angle from the bottom section, (2) a second part that extends and slopes upward and backward from said first part, (3) a third part that extends upward, outward, and forward from the second part and is connected to the second part by a curved or rounded junction 112, and (4) a fourth part connected to and extending forward from the third part to a free top end. The free top end 100 is widened so as to form a pad that overlies the bottom section. As shown in FIG. 21, the second and third parts are spaced substantially farther back than the back edge of the bottom section. The entire second part is higher than the first part, the entire third part is higher than the second part, and the entire fourth part is higher than said third part. The first, second, and third parts are joined by substantially smooth transitions. Each leg has substantially a sheet configuration in which the inner side of each part faces the corresponding opposite side. The outer sides face outwardly away from the member. Also the sides of each part of each leg are oriented generally in parallel to those of the opposite leg, Bottom 1000' has spaced optional notches 1400 and 1410 on the back edge and a centered notch 1405 on the front edge. All notches can be expanded and/or contracted as indicated as indicated by the arrows and dashed lines in FIG. 20 to permit bending and rotation of arms 125 and pads 100.

CONCLUSION, RAMIFICATIONS, AND SCOPE

The embodiments shown of our nasal dilator provide useful and advantageous features. The dilator can be made inexpensively. It can be installed by the untrained wearer. It is rugged, unobtrusive, disposable, and provides a large air path. Two arms surround the air path rather than one, resulting in a stronger dilator that is capable of applying sufficient force to the nostril walls to greatly enhance the wearer's breathing.

While the above description contains many specificities, these should not be considered limiting but merely exemplary. Many variations and ramifications are possible. For example, gases other than air can freely be passed into the user's nose. These can include anesthetics, odorants, and various medications. The dilator can be supplied in any color, or in a combination of colors. Lubrication can be applied to the dilator to facilitate insertion. The dilator can be supplied in or adjusted to non-symmetrical shapes to accommodate noses with non-symmetrical nostrils, or to urge a deviated septum back toward the nasal centerline.

While the present system employs elements which are well known to those skilled in the art of nasal dilator design, it combines these elements in a novel way which produces a new result not heretofore discovered. Accordingly the scope of this invention should be determined, not by the embodiments illustrated, but by the appended claims and their legal equivalents.

The invention claimed is:

1. A nasal dilator for insertion into a person's nostrils for holding said nostrils dilated to facilitate breathing, comprising:
   (a) an elongated, flexible member having a ribbon configuration with two oppositely facing parallel sides that are relatively close together and two opposing edges that are relatively widely spaced, one of said sides being designated an outwardly facing side and the other being designated an inwardly facing side,
   (b) said member bring substantially U-shaped when seen from a front side thereof,
   (c) said member having a generally horizontal and substantially flat bottom section, said inwardly facing side of said bottom section facing upwardly and said outwardly facing surface on said bottom section facing downwardly when said member is inserted into said nostrils, said outwardly and inwardly facing sides of said bottom section being joined by a front edge that faces forwardly from said person and a back edge facing said person when said member is inserted into said nostrils,
   (d) said member having two legs that extend upwardly at from said bottom section so that said legs can be inserted into said person's respective nostrils, said legs each being (a) substantially longer than said bottom section, (b) generally vertically oriented, and (c) having a free upper end,
   (e) each of said legs having four parts as follows when said member is seen from a side thereof:
      (1) a first part that extends upward at a substantially right angle from said bottom section,
      (2) a second part that extends and slopes upward and backward from said first part,
      (3) a third part that extends upward, outward, and forward from said second part and that is connected to said second part by a curved or rounded junction,
      (4) a fourth part connected to and extending forward from said third part to a free top end,
      said free top end being widened so as to form a pad that overlies said bottom section,
   (f) said second and third parts being spaced substantially farther back than said back edge of said bottom section,
   (g) said entire second part being higher than said first part, said entire third part being higher than said second part, and said entire fourth part being higher than said third part,
   (h) said first, second, and third parts being joined by substantially smooth transitions,
   (i) each of said legs having substantially a ribbon configuration with outer and inner sides, said inner sides of opposite legs facing each other, said outer sides of said legs facing outwardly away from said member, each part of leg being oriented generally in parallel to the other leg,
   (j) said member being sized and shaped so that when said legs are inserted into a person's nostrils, said bottom section will contact said person's columella and said free top ends will contact the insides of said person's nostrils and force said nostrils to dilate,
   (k) whereby said member can be facilely inserted into a person's nose with said legs extending into said person's nostrils and said bottom section contacting said person's columella, with said pads urging the outer walls of said person's nose outwardly to expand said nostrils and aid breathing, and said bend defining an air passage to also aid breathing.

2. The nasal dilator of claim 1 wherein said member is made of a material selected from the group consisting of plastic, metal, wood, and a combination of plastic, metal, and wood.

3. The nasal dilator of claim 1 wherein said bottom section has a plurality of notches in said front and back edges thereof to facilitate forming said dilator to conform to a wearer's nose.

4. The nasal dilator of claim 3 wherein said front edge of said bottom section has a single notch therein and said back edge has two notches therein.

5. The nasal dilator of claim 1 wherein said elongated U-shaped flexible member is made of a material selected from the group consisting of plastic, metal, wood, and a combination of plastic, metal, and wood and wherein said bottom section has a plurality of notches in said front and back edges thereof to facilitate forming said dilator to conform to a wearer's nose.

6. The nasal dilator of claim 5 wherein said bottom section has a plurality of notches in said front and back edges thereof to facilitate forming said dilator to conform to a wearer's nose.

7. The nasal dilator of claim 6 wherein said front edge of said bottom section has a single notch therein and said back edge has two notches therein.

8. The nasal dilator of claim 1 wherein bottom or first part of each leg extends up from said bottom section at a generally right angle and parallel to and spaced from the corresponding portion of the other leg.

9. The nasal dilator of claim 1 wherein said first part of each leg also slopes outwardly, away from the corresponding portion of the other leg.

10. A nasal dilator, comprising:
(a) an elongated U-shaped flexible member having a substantially flat bottom section with a front edge and a back edge and two legs that extend up from said bottom section so that said legs can be inserted into said person's respective nostrils, said member having a ribbon configuration with two opposing parallel sides that are relatively close together and that join said two opposing edges, said two opposing edges being relatively widely spaced, one of said sides being designated an outwardly facing side and the other being designated an inwardly facing side,
(b) said legs each being (a) substantially longer than said bottom section, (b) generally vertically oriented, and (c) having a free upper end,
(c) each leg having first, second, third, and fourth parts that extend progressively upward from the said bottom section so that said first part is higher than said bottom section, and each entire succeeding part is higher than its preceding part,
(d) said first part of each leg extending up from said bottom section at a generally right angle and parallel to and spaced from the first part of the other leg,
(e) said second part of each leg being parallel to the second part of the other leg and sloping backwardly at an acute angle to the vertical,
(f) said third part of each leg curving outwardly away from the other leg and curving forwardly,
(g) said first, second, and third parts being joined by substantially smooth transitions,
(h) said second and third parts of each leg joined by a curved or rounded junction,
(i) said fourth part of each leg extending upwardly and then forwardly and widening into a pad, the pad of each leg being substantially parallel to the pad of the other leg,
(j) said second and third parts of each leg being spaced farther back than said back edge of said bottom section,
(k) said dilator being sized and shaped so that said legs can be inserted into a person's nostrils and said bottom section will contact said person's columella,
(l) said first, second, third, and fourth parts of each of said legs having a ribbon configuration with outer and inner sides, said inner side of each section facing the corresponding inner side of the corresponding section of the other leg, said outer sides facing outwardly away from said member, each part of leg being oriented generally in parallel to the corresponding part of the other leg,
(m) whereby said dilator can be inserted into a person's nose with said legs extending into said person's nostrils and said bottom section contacting said person's columella, with said pads urging the outer walls of said person's nose outwardly to expand said nostrils and aid breathing, and bend of said third section defining an air passage to also aid breathing.

11. The nasal dilator of claim 10 wherein said member is made of a material selected from the group consisting of plastic, metal, wood, and a combination of plastic, metal, and wood.

12. The nasal dilator of claim 10 wherein said bottom section has a plurality of notches in said edges thereof to facilitate forming said dilator to conform to a wearer's nose.

13. The nasal dilator of claim 12 wherein said front edge of said bottom section has a single notch therein and said back edge has two notches therein.

14. The nasal dilator of claim 10 wherein said elongated U-shaped flexible member is made of a material selected from the group consisting of plastic, metal, wood, and a combination of plastic, metal, and wood and wherein said bottom section has a plurality of notches in said edges thereof to facilitate forming said dilator to conform to a wearer's nose.

15. The nasal dilator of claim 10 wherein said pads are more widely spaced than said first sections.

16. The nasal dilator of claim 10 wherein said third section or bend of each leg is spaced farther back than said back edge of said bottom section.

17. The nasal dilator of claim 10 wherein said pads overlie said bottom section.

18. The nasal dilator of claim 10 wherein said third section or bend of each leg is spaced farther back than said back edge of said bottom section and said pads overlie said bottom section.

19. The nasal dilator of claim 10 wherein said third section or bend of each leg is spaced farther back than said back edge of said bottom section and said pads overlie said bottom section, and wherein said bottom section has a plurality of notches in said front and back edges thereof to facilitate forming said dilator to conform to a wearer's nose.

20. The nasal dilator of claim 19 wherein said front edge of said bottom section has a single notch therein and said back edge has two notches therein.

* * * * *